(12) United States Patent
Rollins

(10) Patent No.: US 7,950,349 B1
(45) Date of Patent: May 31, 2011

(54) AVIAN EGG FERTILITY AND GENDER DETECTION

(76) Inventor: Jack Dean Rollins, Roswell, GA (US)

( * ) Notice: Subject to any disclaimer, the term of this patent is extended or adjusted under 35 U.S.C. 154(b) by 167 days.

(21) Appl. No.: 12/321,202

(22) Filed: Jan. 17, 2009

Related U.S. Application Data

(60) Provisional application No. 61/011,489, filed on Jan. 18, 2008.

(51) Int. Cl.
*A01K 45/00* (2006.01)
*A01K 43/00* (2006.01)
*G01N 33/08* (2006.01)

(52) U.S. Cl. .............................. 119/6.8; 356/53; 356/66

(58) Field of Classification Search ................ 119/6.8; 356/52–68
See application file for complete search history.

(56) References Cited

U.S. PATENT DOCUMENTS

| | | | |
|---|---|---|---|
| 6,029,080 A | 2/2000 | Reynnells et al. | |
| 6,244,214 B1 * | 6/2001 | Hebrank ....................... | 119/6.8 |
| 6,535,277 B2 * | 3/2003 | Chalker et al. ................ | 356/53 |
| 2002/0157613 A1 * | 10/2002 | Phelps et al. .................. | 119/6.8 |
| 2004/0065263 A1 * | 4/2004 | Hebrank et al. ............... | 119/6.8 |
| 2004/0107912 A1 * | 6/2004 | Hebrank ........................ | 119/6.8 |
| 2007/0041010 A1 * | 2/2007 | Popp et al. .................... | 356/318 |
| 2008/0022931 A1 * | 1/2008 | Mendu et al. ................. | 119/6.8 |

FOREIGN PATENT DOCUMENTS

| | | |
|---|---|---|
| CN | 87 1 07953 A | 8/1988 |
| EP | 0 430 150 A2 | 6/1991 |
| WO | WO 2004/096971 A2 | 11/2004 |

OTHER PUBLICATIONS

Alexis L. Romanoff, Stimulating Effects of Ultraviolet Radiation on Bioelectric Potentials of an Avian Egg, 1943, pp. 123-126, Agricultural Experiment Station, Cornell University, Ithaca, New York.

Niggli et al., Laser-Ultraviolet-A-Induced Ultraweak Photon Emission in Mammalian Cells, Journal, Mar./Apr. 2005, vol. 10(2), pp. 024006-1-024006-6, Journal of Biomedical Optics.

Belousov et al., Ultraweak Emission of Chick Eggs and Embryos: Nonadditive Interaction of Two Emitters and Stable Nonequilibricity, 1997, vol. 28, No. 5, pp. 310-320, Russian Journal of Dvelopmental Biology.

(Continued)

*Primary Examiner* — Kimberly S Smith
*Assistant Examiner* — Joshua Huson
(74) *Attorney, Agent, or Firm* — Alston & Bird LLP

(57) ABSTRACT

Following exposure to an external light source, determining: 1) the fertility of an avian egg by measuring the photon intensity (photons per second) of the egg's biophoton and luminescence; and 2) the gender of an avian egg by measuring the photon spectrum of the egg's biophoton emission and luminescence. The external light source is either an incandescent, fluorescent, LED, (pulsed or continuous wave) monochromatic or dichromatic laser light source. The detector of the photon intensity is either a low light sensing photomultiplier tube (PMT), silicon based photon counting sensor, or Geiger-mode avalanche photodiode detector. The detector of the photon spectrum is a spectrometer. Following exposure to the referenced light sources, fertile avian eggs will exhibit a higher intensity of photons than that of unfertilized avian eggs, and avian eggs of the female gender will emit a different spectrum of photons than will avian eggs of the male gender.

13 Claims, 1 Drawing Sheet

OTHER PUBLICATIONS

Beloussov et al., Biophoton Emission From Developing Eggs and Embryos: Non-Linearity, Wholistic Properties and Indications of Energy Transfer, 1998, pp. 121-123, 130-31, Kluwer Academic Publishers, Netherlands.

L.V. Beloussov, Biophotonics, Non-Equilibrium and Coherent Systems in Biology, Biophysics and Biotechnology, Photon-Emitting Properties of Developing Hen Eggs, 1995, 15 pages total, Bioinform Services Co, Russia.

Niggli et al., Biophotonics Optical Science and Engineering for the 21st Century, Laser-Ultraviolet-A Induced Biophotonic Emission in Cultured Mammalian Cells, 2005, Chapter 14, 7 Pages, Springer, United States.

* cited by examiner

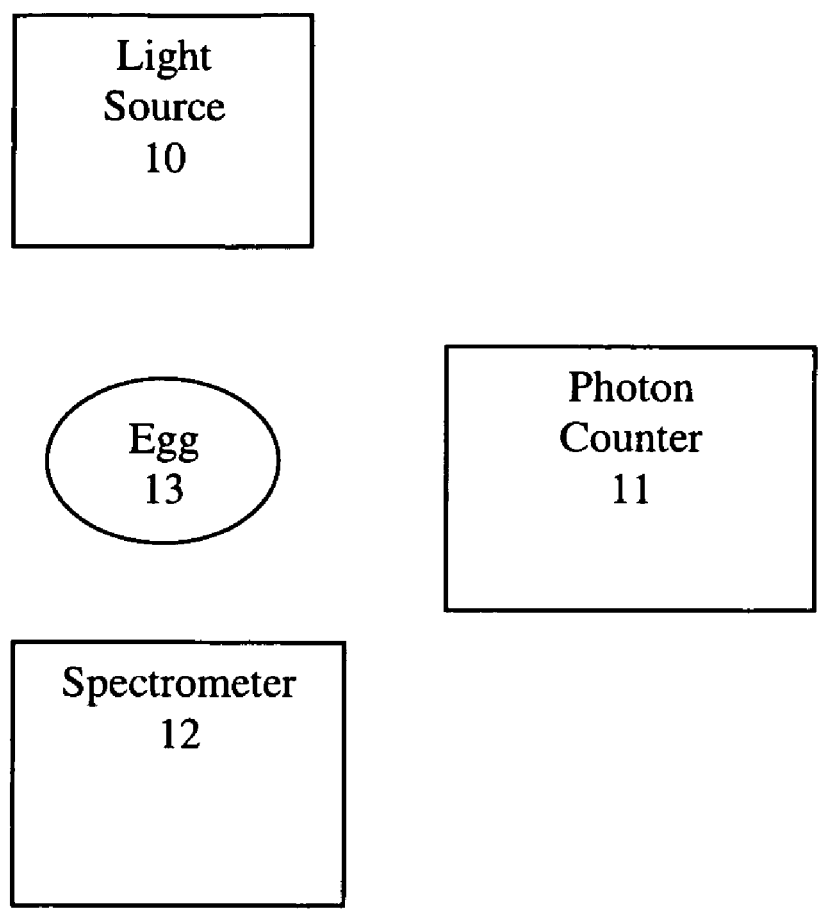

AVIAN EGG FERTILITY AND GENDER DETECTION

CROSS-REFERENCE TO RELATED APPLICATIONS

This application claims the benefit of PPA Ser. No. 61/011,489, filed Jan. 18, 2008 by the present inventor, which is incorporated by reference.

BACKGROUND OF THE INVENTION

1. Field

This application relates to avian eggs, specifically an improved method of detecting the fertility and gender of avian eggs.

2. Prior Art

Previously, methods to detect avian egg fertility, such as candling, were only feasible after the egg had been incubated for several days, thereby limiting the economic advantage of such an approach. Also, invasive methods to detect avian egg gender, such as analytical detection of estrogenic compounds present in the egg's allantoic fluid, required 13 to 18 days of incubation. The real economic advantage to avian egg fertility and gender detection would be to make the detection at the pre-incubation stage thereby allowing the eggs to be segregated and processed separately. For example, in the poultry industry male leghorn chicks are killed upon hatching since they can't produce eggs; and in the broiler (meat-producing) industry male eggs are preferred to place in incubation because they grow much faster than female eggs. The existing technologies are either not applicable to egg segregation at the pre-incubation stage, or else do not permit a sufficiently accurate fertility/gender detection as to be economically feasible.

SUMMARY

The invention consists of a method to determine: 1) the fertility of an avian egg by measuring the photon intensity (photons per second) of the egg's biophoton and luminescence following exposure to an external light source; and 2) the gender of an avian egg by measuring the photon spectrum of the egg's biophoton emission and luminescence following exposure to an external light source. The external light source is either an incandescent, fluorescent, LED, (pulsed or continuous wave) monochromatic or dichromatic laser light source. The detector of the photon intensity is either a low light sensing photomultiplier tube (PMT), silicon based photon counting sensor, or Geiger-mode avalanche photodiode detector. The detector of the photon spectrum is a spectrometer. The first part of the invention derives from the fact that following exposure to the referenced light sources, fertile avian eggs will exhibit a higher intensity of photons than that of unfertilized avian eggs. The second part of the invention derives from the fact that following exposure to the referenced light sources, avian eggs of the female gender will emit a different spectrum of photons than will avian eggs of the male gender, thereby allowing one to distinguish between avian eggs of female and male gender.

DRAWINGS

Figures

FIG. 1 is an overview of the invention.

REFERENCE NUMERALS

| | |
|---|---|
| 10 | Light Source |
| 11 | Photon Counter |
| 12 | Spectrometer |
| 13 | Egg |

DETAILED DESCRIPTION

The static physical structure of the invention consists of three major components, i.e., a specially selected light source, a photon counter and a spectrometer which may or may not be connected to a power source and computer display.

OPERATION

The light source (10) bio-stimulates the egg to emit a higher than normal flux of biophotons, and delayed luminescence. The photon detector (11) measures (counts) the photon emission from the egg (13). The spectrometer (12) measures the spectrum of the photon emission. Egg fertility is determined by the difference in the emitted photon flux of the fertile and unfertile eggs that is registered by the photon detector (11). Distinction between the two types of eggs is made possible by the higher simulation of the fertile egg that results from the light stimulation. The difference in photon intensities of the light-stimulated fertile and unfertile eggs is sufficiently high to make the technology applicable to pre-incubated eggs. Egg gender is determined by the difference in the emitted photon spectrum of the female and male eggs that is registered by the spectrometer (12).

CONCLUSION, RAMIFICATIONS, AND SCOPE

Thus, the reader will see that the embodiment of the detection system provides a unique and unprecedented method of determining avian egg fertility and gender at the pre-incubated stage. The detection system components can vary as follows:

The light source can vary in wavelength
The light source can vary in intensity
The light source can vary in mode (pulsed or continuous)
The light source can vary in sequence (monochromatic or dichromatic)
The light source can vary in polarity (right circularity polarity or left circular polarity through as quartz prism filter)
The light source (if laser) can be linear or non-linear
The photon counter can be either:
 A low light sensing photomultiplier tube (PMT)
 A silicon based photon counting sensor
 A Geiger-mode avalanche photodiode detector
 Any low light sensing device with sufficient sensitivity The spectrometer can vary in:
  Wavelength applicability
  The arrangement and electrical connection of the system components can be varied
  The components can be connected to a computer for output display purposes

I claim:

1. A method of distinguishing unfertile pre-incubated eggs from fertile pre-incubated eggs, comprising:
  stimulating biophoton and delayed luminescence emissions from a plurality of pre-incubated avian eggs;
  measuring the intensity of biophoton and delayed luminescence emissions from each of the plurality of eggs;
  comparing the measured biophoton and delayed luminescence emissions; and
  classifying eggs having a relatively higher intensity of biophoton emissions and delayed luminescence as fertile and eggs having a relatively lower intensity of biophoton and delayed luminescence emissions as unfertile.

2. The method of claim 1, wherein the stimulating step comprises exposing the plurality of pre-incubated avian eggs to illumination from a pulsed monochromatic or dichromatic laser.

3. The method of claim 2, wherein the laser is a linear or a non-linear laser.

4. The method of claim 1, wherein the stimulating step comprises exposing the plurality of pre-incubated avian eggs to laser illumination that is right-circular polarized using a quartz crystal prism.

5. The method of claim 1, wherein the stimulating step comprises exposing the plurality of pre-incubated avian eggs to illumination from a continuous wave monochromatic or dichromatic laser.

6. The method claim 1, wherein the biophoton and delayed luminescence intensity is measured by a photomultiplier tube, a silicon based photon counting sensor, or a Geiger-mode avalanche photodiode detector.

7. A method for detecting the gender of pre-incubated avian eggs comprising:
  stimulating biophoton and delayed luminescence emissions from a plurality of pre-incubated avian eggs;
  measuring the spectrum of biophoton and delayed luminescence emissions from each of the plurality of eggs;
  comparing the measured spectra of biophoton and delayed luminescence emissions; and
  classifying eggs having a first spectrum of biophoton and delayed luminescence emissions as having a first gender and eggs having a second spectrum different from the first spectrum of biophoton and delayed luminescence emissions as having a second gender.

8. The method of claim 7, wherein the stimulating step comprises exposing the plurality of pre-incubated avian eggs to illumination from a pulsed monochromatic or dichromatic laser.

9. The method of claim 8, wherein the laser is a linear or a non-linear laser.

10. The method of claim 7, wherein the stimulating step comprises exposing the plurality of pre-incubated avian eggs to laser illumination that is right-circular polarized using a quartz crystal prism.

11. The method of claim 7, wherein the stimulating step comprises exposing the plurality of pre-incubated avian eggs to illumination from a continuous wave monochromatic or dichromatic laser.

12. The method of claim 7, wherein the biophoton and delayed luminescence spectra are measured by a spectrometer.

13. A method for simultaneously detecting the fertility and gender of pre-incubated avian eggs comprising:
  exposing a plurality of pre-incubated avian eggs to illumination from a pulsed or continuous wave monochromatic or dichromatic laser to stimulate biophoton and delayed luminescence emissions of the eggs;
  measuring the intensity and spectrum of biophoton and delayed luminescence emissions from each of the plurality of eggs;
  comparing the measured biophoton and delayed luminescence emissions; classifying eggs having a relatively higher intensity of biophoton and delayed luminescence emissions as fertile and eggs having a relatively lower intensity of biophoton and delayed luminescence emissions as unfertile; and
  classifying eggs having a first spectrum of biophoton and delayed luminescence emissions as having a first gender and eggs having a second spectrum different from the first spectrum of biophoton and delayed luminescence emissions as having a second gender.

* * * * *